United States Patent [19]

Nishikata et al.

[11] Patent Number: 5,616,802
[45] Date of Patent: Apr. 1, 1997

[54] CYCLOBUTENEDIONE DERIVATIVE, PROCESS FOR PREPARING THE SAME, AND NONLINEAR OPTICAL ELEMENT

[75] Inventors: Yasunari Nishikata; Lyong Sun Pu, both of Ebina, Japan

[73] Assignee: Fuji Xerox Co., Ltd., Tokyo, Japan

[21] Appl. No.: 421,875

[22] Filed: Apr. 14, 1995

[30] Foreign Application Priority Data

Oct. 19, 1994 [JP] Japan .................................. 6-253717

[51] Int. Cl.⁶ .................................................. C07C 211/16
[52] U.S. Cl. .......................................... 564/307; 359/328
[58] Field of Search ............................................. 564/307

[56] References Cited

U.S. PATENT DOCUMENTS

| | | |
|---|---|---|
| 4,986,935 | 1/1991 | Ageishi et al. . |
| 5,106,997 | 4/1992 | Pu . |
| 5,210,302 | 5/1993 | Pu . |

FOREIGN PATENT DOCUMENTS

| | | |
|---|---|---|
| 1-204031 | 8/1989 | Japan . |
| 2-259735 | 10/1990 | Japan . |
| 3-71117 | 3/1991 | Japan . |
| 3-112950 | 5/1991 | Japan . |
| 3-112961 | 5/1991 | Japan . |
| 4-199135 | 7/1992 | Japan . |
| 4-202165 | 7/1992 | Japan . |
| 4-202166 | 7/1992 | Japan . |
| 4-202167 | 7/1992 | Japan . |
| 5-229999 | 9/1993 | Japan . |
| 5-281587 | 10/1993 | Japan . |
| 5-310655 | 11/1993 | Japan . |
| 6-82857 | 3/1994 | Japan . |
| 6-100511 | 4/1994 | Japan . |
| 6-175178 | 6/1994 | Japan . |
| 6-306027 | 11/1994 | Japan . |

OTHER PUBLICATIONS

The America Physical Society 1991, Physical Review Letters, "Hyper–Rayleigh Scattering in Solution", Jun. 10, 1991, vol. 66, No. 23, Koen Clays et al. pp. 2980–2983.

*Primary Examiner*—D. R. Wilson
*Attorney, Agent, or Firm*—Oliff & Berridge

[57] ABSTRACT

The present invention provides a novel chemical substance for practical organic nonlinear optical element having a great nonlinear optical effect, an excellent chemical and thermal stability and transparency which can easily undergo crystalline growth from a liquid phase or melt phase and can be easily worked, a process for the preparation thereof, and a nonlinear optical element prepared from such a material. A novel cyclobutenedione derivative prepared in accordance with the following reaction formula, a process for the preparation thereof, and a nonlinear optical element comprising such a derivative are provided:

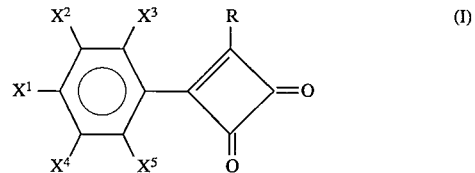

wherein $X^1$ represents a halogen atom; $X^2$, $X^3$, $X^4$ and $X^5$ each represent a hydrogen atom or a halogen atom; and R represents a substituent represented by the following formula:

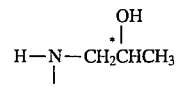

wherein C* represents an asymmetric carbon atom.

4 Claims, 1 Drawing Sheet

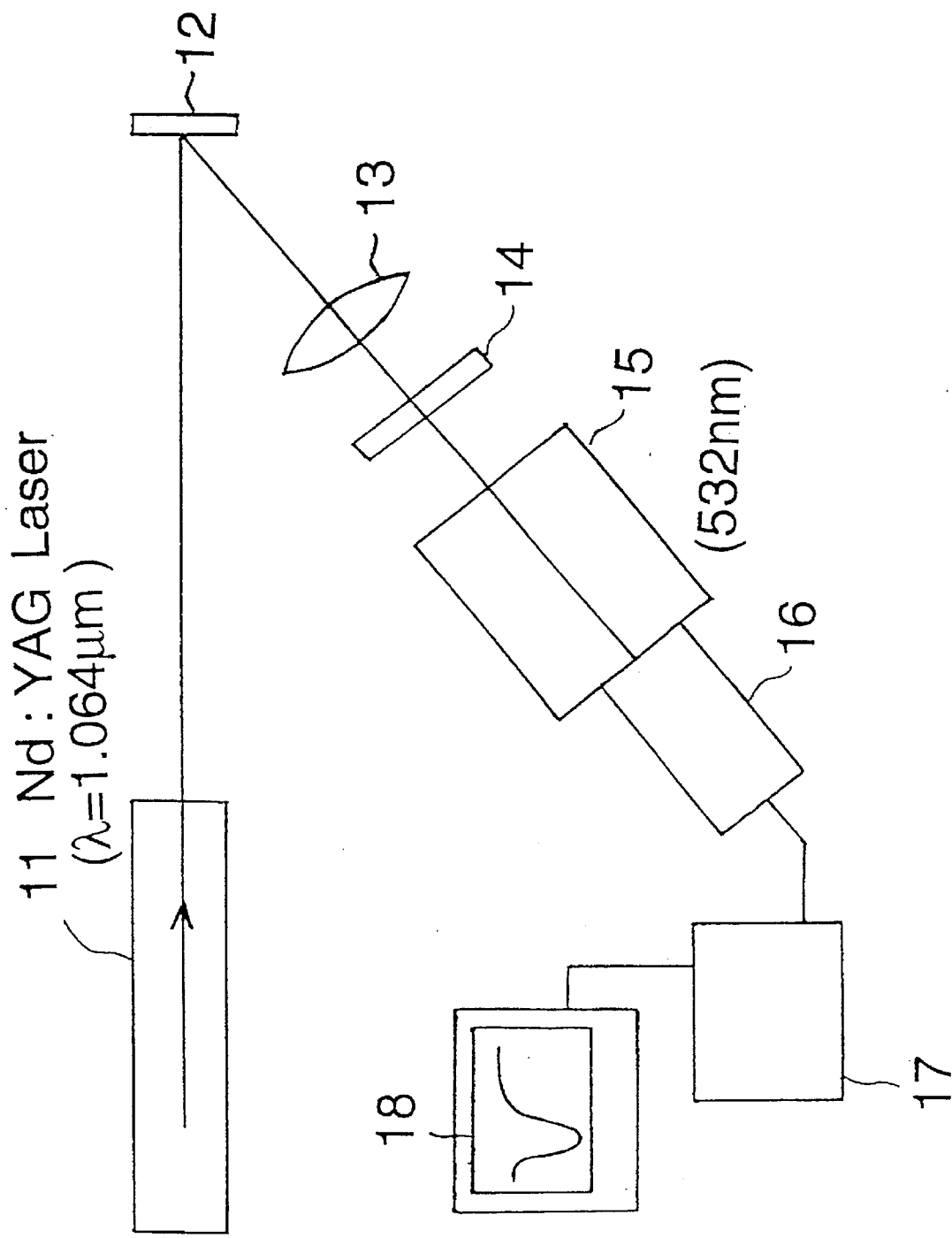

CYCLOBUTENEDIONE DERIVATIVE, PROCESS FOR PREPARING THE SAME, AND NONLINEAR OPTICAL ELEMENT

FIELD OF THE INVENTION

The present invention relates to a novel cyclobutenedione derivative which can be used as a nonlinear optical material. More particularly, the present invention relates to a process for the preparation of such a cyclobutenedione derivative. The present invention further relates to a nonlinear optical element comprising such a cyclobutenedione derivative.

BACKGROUND OF THE INVENTION

A nonlinear optical element plays an important role in the field of optical communications and optical information processing. A nonlinear optical material for nonlinear optical element is a substance which exerts extremely important effects in the processing of optical signal. For example, it can exert an optical mixing effect to generate a frequency representative of the sum or difference of two incident lights having different frequencies. It also exerts an optical parametric effect to emit light having a frequency different from the original frequency. It further exerts Pockels effect or Kerr effect due to the change in the refractive index of light medium. Further, it can convert incident light into second harmonic (SHG) or third harmonic (THG). Moreover, it exerts a memory effect due to optical bistability.

As the nonlinear optical element material there has heretofore been mainly used an inorganic compound. As such an inorganic nonlinear optical material there has been known an inorganic compound such as potassium titanium phosphate (KTP: $KTiOPO_4$) and lithium niobate (LN: $LiNbO_3$) in crystal form. However, one of these inorganic compounds can satisfy the requirements in the foregoing applications.

On the other hand, an organic nonlinear optical material has recently been noted as a new optical element material in the field of optoelectronics and extensively studied. In particular, it has been known that a compound having an electron donative group and an electron attractive group in π-electron conjugated system undergoes an interaction between laser beam as electromagnetic wave and π-electron unevenly distributed in the molecule to exhibit a strong optical nonlinearity at the molecular level (on a molecular basis).

Examples of compounds which have been studied include 2-methyl-4-nitroaniline, m-nitroaniline, N-(4-nitrophenyl)-L-prolinol, 4-dimethylamino-4'-nitrostilbenzene, and 4'-nitrobenzylidene-4-nitroaniline.

Most of these materials are used in the form of single crystal similarly to the inorganic materials. These single crystals need to be noncentrosymmetric to exert secondary optical nonlinearity effect. However, since these materials have a high molecular dipole moment, the noncentrosymmetric crystals can hardly form a thermodynamically stable phase.

Referring to the design of a material which forms an noncentrosymmetric crystal, the introduction of asymmetric centers or the use of hydrogen bonds has been known useful. However, ordinary methods have not been found yet.

Further, problems characteristic of organic materials, i.e., difficulty in crystal growth and fragility of the resulting crystal, make it difficult to precision-process these crystals. It has thus been keenly desired to put into practical use of a high performance material necessary for the preparation of high efficiency elements.

In general, a nonlinear optical element is required to exhibit a high optical nonlinearity, an excellent workability, heat resistance, weathering stability and optical transparency, and a high breakdown voltage and stability upon irradiation with laser beam in combination. However, it is extremely difficult to select from conventional known materials those satisfying these requirements.

The inventors previously proposed cyclobutenedione derivatives represented by the general formula (IV) shown below and nonlinear optical elements comprising these cyclobutenedione derivatives (see JP-A-3-112950 (The term "JP-A" as used herein means an "unexamined published Japanese patent application")). These derivatives are characterized by optical nonlinearity extremely greater than that of known materials. However, these derivatives are disadvantageous in that they exhibit a maximum absorption value (λmax) as great as about 400 nm and thus are not suitable for the generation of second harmonics from a semiconductor laser (oscillation wavelength: 700–800 nm). It has thus been desired to provide a material having a better transparency to visible light.

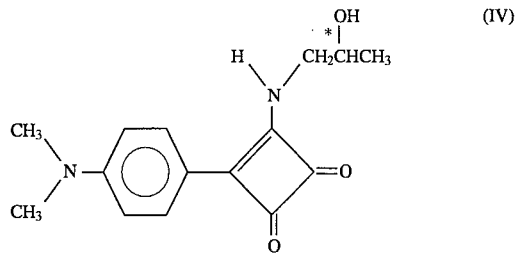

SUMMARY OF THE INVENTION

It is therefore an object of the present invention to provide a novel chemical substance suitable for the preparation of a practical organic nonlinear optical element having a high nonlinear optical effect, and an excellent chemical and thermal stability, transparency, and workability, and crystallizability from liquid phase and melt phase.

It is another object of the present invention to provide a process for the preparation of such a chemical substance.

It is a further object of the present invention to provide a nonlinear optical element prepared from such a material.

These and other objects of the present invention will become more apparent from the following detailed description and examples.

The inventors have found that the introduction of appropriate substituents into a compound having a high molecular dipole moment which can easily form a centrosymmetric structure upon crystallization makes it possible to obtain a compound having a high secondary nonlinear optical effect and confirmed that the resulting compound can be applied to organic nonlinear optical elements. Thus, the present invention has been worked out.

The first aspect of the present invention is a cyclobutenedione derivative, represented by the following formula (I)

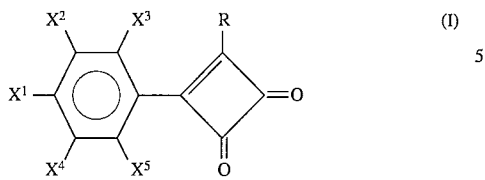

wherein $X^1$ represents a halogen atom; $X^2$, $X^3$, $X^4$ and $X^5$ each represents a hydrogen atom or a halogen atom; and R represents a substituent represented by the following formula

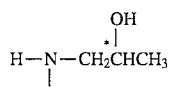

wherein C* represents an asymmetric carbon atom (preferably having R- or S-configuration, preferably R-configuration).

The second aspect of the present invention is a cyclobutenedione derivative, represented by the following formula (II)

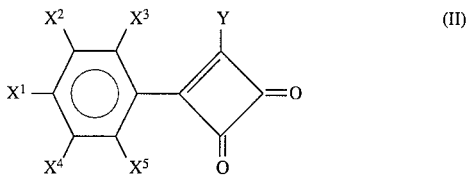

wherein Y represents a chlorine atom, a bromine atom, a methoxy group or an ethoxy group; $X^1$ represents a halogen atom; and $X^2$, $X^3$, $X^4$ and $X^5$ each represents a hydrogen atom or a halogen atom.

The third aspect of the present invention is a process for the preparation of a cyclobutenedione derivative represented by formula (I) defined above, which comprises reacting a cyclobutenedione derivative represented by formula (II) defined above with an asymmetric 1-amino-2-propanol represented by the following formula (III)

wherein C* represents an asymmetric carbon atom.

The fourth aspect of the present invention is a nonlinear optical element, prepared from a cyclobutenedione derivative represented by formula (I) defined above.

BRIEF DESCRIPTION OF THE DRAWING

By way of example and to make the description more clear, reference is made to the accompanying drawing in which:

The attached figure is a block diagram illustrating an optical system for measuring the optical nonlinearity (SHG activity) of a sample.

DETAILED DESCRIPTION OF THE INVENTION

The inventors made studies of organic compounds suitable for use in nonlinear optical element, including the previously proposed cyclobutenedione derivatives. As a result, it has been found that the cyclobutenedione derivative represented by the foregoing formula (I) has a relatively high optical nonlinearity, exhibits absorption at a short wavelength range and shows superior light transmission properties to the previously proposed cyclobutenedione derivatives. The present invention has been worked out.

The cyclobutenedionyl group contained in the cyclobutenedione derivative represented by the foregoing formula (I) has a strong interaction with π electron in the compound and thus exhibits a strong electron-withdrawing property due to resonance effect as can be seen in the maximum absorption wavelength (intramolecular charge transfer absorption band) shown in the examples described later. Therefore, the cyclobutenedione derivative represented by the foregoing formula (I) is apt to have a structure in which the molecule is electrically strongly polarized and thus can exhibit a high optical nonlinearity. In other words, although the halogen atoms contained in the various examples exhibit a small electron donation as compared with an amino group, an alkoxy group, an alkylthio group or other groups which are well known, these compounds exhibit a second supramolecular polarizability as extremely great as 1.2 times that of paranitroaniline materials.

Further, the cyclobutenedione derivative of formula (I) comprises an asymmetric carbon atom-containing aminoalcohol incorporated therein as a substituent. This substituent makes it possible to control the molecular orientation in the crystal by its steric structure and hydrogen bond. This substituent also allows a molecule having a large dipole moment to be oriented centrosymmetrically, facilitating the growth of a crystal having a great optical nonlinearity.

The cyclobutenedione derivative of formula (I) preferably has a second supramolecular polarizability (in methanol) of about not less than $30 \times 10^{-30}$ esu and show a good transmission property. The cyclobutenedione derivative of formula (I) preferably has a λmax of 350 nm or less.

The cyclobutenedione derivative of formula (I) can be easily synthesized in a good yield in accordance with the following reaction formula

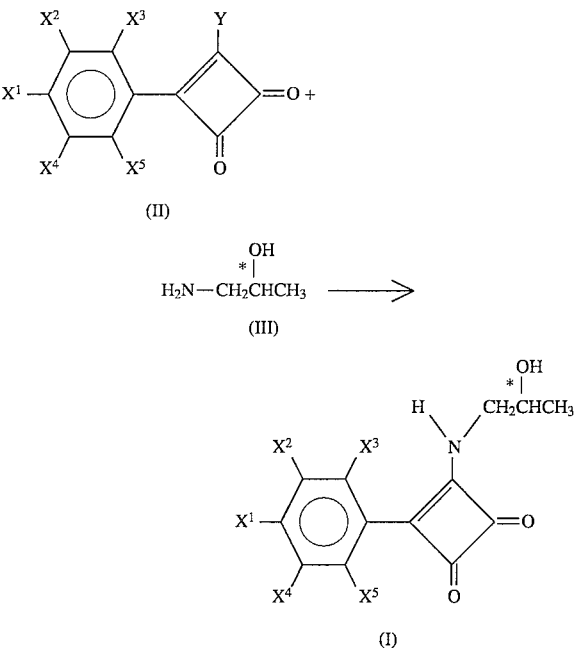

wherein Y represents a chlorine atom, a bromine atom, a methoxy group or an ethoxy group; $X^1$ represents a halogen atom; and $X^2$, $X^3$, $X^4$ and $X^5$ each represents a hydrogen atom or a halogen atom. Y is preferably a methoxy group or an ethoxy group from the standpoint of yield for preparing the cyclobutenedione derivative of formula (I).

In some detail, the cyclobutenedione derivative represented by the foregoing formula (II) is first dispersed or suspended in a solvent such as acetone, tetrahydrofuran, dichloromethane, chloroform, methanol, ethanol, N,N-dimethylformamide, N,N-dimethylacetamide and dimethyl sulfoxide. To the resulting solution or suspension is then added gradually asymmetric 1-amino-2-propanol in an amount not less than equal to that of the cyclobutenedione derivative to effect reaction. In general, the reaction rapidly proceeds at room temperature. If necessary, the reaction can be accelerated by heating.

Further, if Y in formula (II) is a chlorine atom or a bromine atom, a proper acid binder, that is, a basic compound such as triethylamine, N-methyl morpholine and sodium carbonate may be present in the system to accelerate the reaction. If products are precipitated as the reaction proceeds, they are filtered off. On the other hand, if no products are precipitated, products can be precipitated by the concentration of the reaction solution, the addition of a proper noble solvent thereto, or other means. The resulting crystal can be optionally recrystallized from a solvent such as alcohol and acetone or purified by sublimation.

Instead of the foregoing asymmetric 1-amino-2-propanol, its salt with acid such as hydrochloride, hydrobromide and p-toluenesulfonate may be used as a raw material. It is then reacted with the cyclobutenedione derivative represented by the foregoing formula (II) in the presence of a basic compound such as triethylamine, N-methyl morpholine and sodium carbonate in the same manner as mentioned above to effect synthesis.

The cyclobutenedione derivative represented by the foregoing formula (II) can also be prepared by subjecting 1,2-dichloro-cyclobutene-3,4-dione to Friedel-Crafts reaction with stirring in a corresponding Friedel-Crafts solvent such as halobenzene (e.g., carbon disulfide, nitrobenzene, dichloromethane, 1,2-dichloromethane) or by reacting 1,2-dihydroxy-cyclobutene-3,4-dione with a corresponding halobenzene in the presence of a trialkyloxonium salt in a solvent for halogenation.

The compound represented by formula (I) of the present invention contains cyclobutenediones which exhibit a very strong withdrawing property with each other and has a long electron conjugated system. In other words, such a compound has its molecule electrically strongly polarized. When this structure is stabilized, this compound exhibits a high optical nonlinearity.

Since the compound represented by formula (I) comprises an amine derivative having an asymmetric carbon atom and a hydrogen bonding capacity incorporated therein as R, it exhibits a high optical nonlinearity, though being a molecule having a large dipole moment in the ground state.

Further, the compound represented by the general formula (I) of the present invention exhibits an excellent heat resistance, weathering resistance, transparency, durability and workability, it can be used as a material for nonlinear optical element.

The present invention will be further described in the following examples, but the present invention should not be construed as being limited thereto.

EXAMPLE 1

Synthesis of
1-chloro-2-(4-fluorophenyl)-cyclobutene-3,4-dione
[structural formula (II-1)]

15 g (about 0.1 mol) of 1,2-dichloro-cyclobutene-3,4-dione were dissolved in 40 ml of 1,2-dichloroethane. To the solution were then added 13 g (about 0.1 mol) of aluminum chloride. The reaction mixture was then heated under reflux for 1.5 hours. The system was cooled to a temperature of 20° C. To the reaction system was then added dropwise 9.5 g (about 0.1 mol) of fluorobenzene. After the completion of dropwise addition, the mixture was further stirred at room temperature for 3 hours to cause the reaction to proceed in accordance with the following reaction formula:

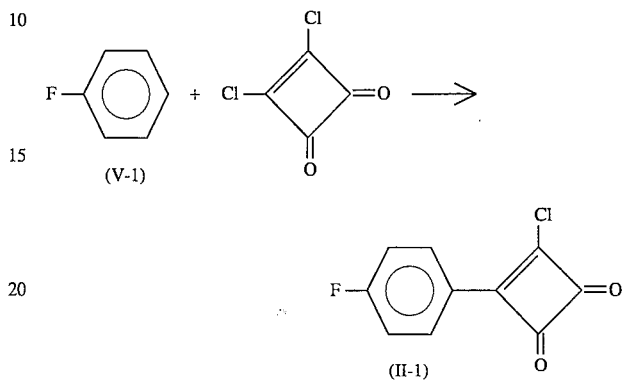

After the completion of the reaction, the reaction system was cooled. To the reaction system were then added 50 ml of cold water. The reaction system was then stirred for 10 minutes. The resulting phase was separated, and then dried over anhydrous magnesium sulfate. The magnesium sulfate was then filtered off. The filtrate was then concentrated until the total amount of the system reached 20 ml. To the system were then added about 30 ml of n-hexane. The system was then cooled to a temperature of −20° C. The resulting crystal was recovered by filtration, and then dried to obtain 4.5 g of 1-chloro-2-(4-fluorophenyl)-cyclobutene-3,4-dione represented by the structural formula (II-1) shown below. The yield was 21%. The product of the structural formula (II-1) exhibited maximum absorption wavelengths (λmax) of 322.6 nm and 333.5 nm in the form of methylene chloride solution.

Melting point: 113°–115° C.

Elementary analysis:

Calculated %: C 57.03, H 1.91, halogen 25.86

Found %: C 56.91, H 2.03, halogen 25.58

EXAMPLE 2

Synthesis of
1-ethoxy-2-(4-fluorophenyl)-cyclobutene-3,4-dione
[structural formula (I-2)]

At the end of the reaction shown in Example 1, the reaction system was poured into 50 ml of ethanol which had been cooled to a temperature of 0° C. The reaction system was then entirely kept at a temperature of −20° C. overnight. The resulting crystal was recovered by filtration, and then dried to obtain 15 g of 1-ethoxy-2-(4-fluorophenyl)-cyclobutene-3,4-dione. The yield was 71%. The product of the structural formula (II-2) exhibited maximum absorption wavelengths (λmax) of 322.3 nm and 336.5 nm in the form of methylene chloride solution.

Melting point: 126°–129° C.

Elementary analysis:

Calculated %: C 65.46, H 4.12, halogen 8.63
Found %: C 65.20, H 4.93, halogen 8.38

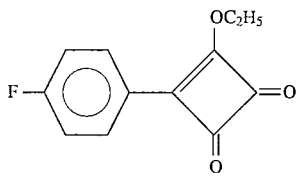
(II-2)

EXAMPLES 3–7

Intermediate products (II-3 to II-7) set forth in Tables 1 and 2 were synthesized in the same manner as in Example 1 except that as the starting materials there were used halobenzene derivatives (V-2 to V-6) set forth in Tables 1 and 2, respectively. These intermediate products were measured for melting point and maximum absorption wavelength ($\lambda$max) in the form of methanol solution. The results are set forth in Table 3. The results of elementary analysis are set forth in Table 3.

EXAMPLES 8–12

Intermediate products (II-8 to II-12) set forth in Tables 1 and 2 were synthesized in the same manner as in Example 2 except that as the starting materials there were used halobenzene derivatives (V-2 to V-6) set forth in Tables 1 and 2, respectively. These intermediate products were measured for melting point and maximum absorption wavelength ($\lambda$max) in the form of methanol solution. The results are set forth in Table 3.

TABLE 1

| Example No. | Starting material (V) | | Intermediate product (II) | |
| --- | --- | --- | --- | --- |
| Example 1 | F–⟨phenyl⟩ | (V-1) | F–⟨phenyl⟩–squarate(Cl) | (II-1) |
| Example 2 | F–⟨phenyl⟩ | (V-1) | F–⟨phenyl⟩–squarate(OC₂H₅) | (II-2) |
| Example 3 | Cl–⟨phenyl⟩ | (V-2) | Cl–⟨phenyl⟩–squarate(Cl) | (II-3) |
| Example 4 | Br–⟨phenyl⟩ | (V-3) | Br–⟨phenyl⟩–squarate(Cl) | (II-4) |
| Example 5 | I–⟨phenyl⟩ | (V-4) | I–⟨phenyl⟩–squarate(Cl) | (II-5) |
| Example 6 | Cl,Cl–⟨phenyl⟩ | (V-5) | Cl,Cl–⟨phenyl⟩–squarate(Cl) | (II-6) |

TABLE 2

| Example No. | Starting material (V) | | Intermediate product (II) | |
|---|---|---|---|---|
| Example 7 | 1,3-dichlorobenzene | (V-6) | 3-chloro-4-(2,4-dichlorophenyl)-3-cyclobutene-1,2-dione | (II-7) |
| Example 8 | chlorobenzene | (V-2) | 3-ethoxy-4-(4-chlorophenyl)-3-cyclobutene-1,2-dione | (II-8) |
| Example 9 | bromobenzene | (V-3) | 3-ethoxy-4-(4-bromophenyl)-3-cyclobutene-1,2-dione | (II-9) |
| Example 10 | iodobenzene | (V-4) | 3-ethoxy-4-(4-iodophenyl)-3-cyclobutene-1,2-dione | (II-10) |
| Example 11 | 1,2-dichlorobenzene | (V-5) | 3-ethoxy-4-(3,4-dichlorophenyl)-3-cyclobutene-1,2-dione | (II-11) |
| Example 12 | 1,3-dichlorobenzene | (V-6) | 3-ethoxy-4-(2,4-dichlorophenyl)-3-cyclobutene-1,2-dione | (II-12) |

TABLE 3

| Intermediate product | λmax (nm) | m.p.* (°C.) | Elementary analysis (%) C | H | Halogen |
|---|---|---|---|---|---|
| II-1 | 322.6 | 113° C.–115° C. | 56.91 (57.03) | 2.03 (1.91) | 25.58 (25.86) |
| II-2 | 322.3 | 126° C.–129° C. | 65.20 (65.46) | 4.93 (4.12) | 8.38 (8.63) |
| II-3 | 328.2 | 134° C.–139° C. | 52.62 (52.90) | 1.80 (1.78) | 31.01 (31.23) |
| II-4 | 329.5 | 145° C.–147° C. | 44.08 (44.24) | 1.55 (1.49) | 41.98 (42.49) |
| II-5 | 328.3 | 113° C.–115° C. | 37.45 (37.71) | 1.30 (1.27) | 50.64 (50.98) |
| II-6 | 302.7 | 157° C.–160° C. | 45.77 (45.93) | 0.99 (1.16) | 40.38 (40.67) |
| II-7 | 297.4 | 75° C.–79° C. | 45.81 (45.93) | 1.13 (1.16) | 40.52 (40.67) |
| II-8 | 329.0 | 110° C.–114° C. | 60.75 (60.96) | 3.88 (3.83) | 14.69 (14.98) |
| II-9 | 329.8 | 104° C.–109° C. | 51.07 (51.27) | 3.18 (3.23) | 28.60 (28.42) |
| II-10 | 328.1 | 138° C.–144° C. | 43.68 (43.93) | 2.55 (2.76) | 36.88 (36.68) |
| II-11 | 310.6 | 145° C.–151° C. | 52.98 (53.17) | 2.88 (2.97) | 25.97 (26.16) |
| II-12 | 300.3 | 85° C.–91° C. | 53.02 (53.17) | 3.01 (2.97) | 26.22 (26.16) |

(The figures in the parentheses indicate calculated values)

EXAMPLE 13

Synthesis of 1-(4-fluorophenyl)-2-[(R)-2-hydroxypropylamino]-cyclobutene-3,4-dione [structural formula (I-1)]

To a suspension of 1 g (4.4 mmol) of a compound represented by the following structural formula (II-2) in 5 ml of methanol were added dropwise 0.8 g (about 10 mmol) of (R)-(−)-1-amino-2-propenol to effect reaction in accordance with the following reaction formula:

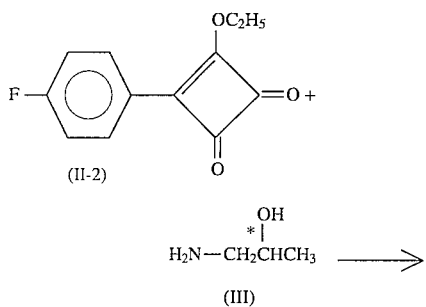

After the completion of the reaction, the reaction solution was poured into water to precipitate a white crystal which was then recovered by filtration to obtain 0.9 g of 1-(4-fluorophenyl)-2-[(R)-2-hydroxypropylamino]-cyclobutene-3,4-dione. The yield was 83%. The elementary analysis and melting point of the crystal thus obtained are set forth below. The crystal exhibited maximum absorption wavelengths (λmax) of 335.5 nm and 322.6 nm.

Melting point: 235°–237° C.

Elementary analysis:

Calculated %: C 62.65, H 4.85, N 5.62, halogen 7.62
Found %: C 62.35, H 4.94, N 5.48, halogen 7.49

This compound (1-(4-fluorophenyl)-2-[(R)-2-hydroxypropylamino]-cyclobutene-3,4-dione) could be also obtained in the form of white crystal represented by the following structural formula by adding dropwise 0.8 g (about 10 mmol) of (R)-(−)-1-amino-2-propenol to 5 ml of a methylene chloride solution containing 1 g (4.4 mmol) of a compound represented by the following structural formula (II-1) to effect reaction in accordance with the following reaction formula, and then pouring the reaction solution into a 50° C. water. The yield was 7%.

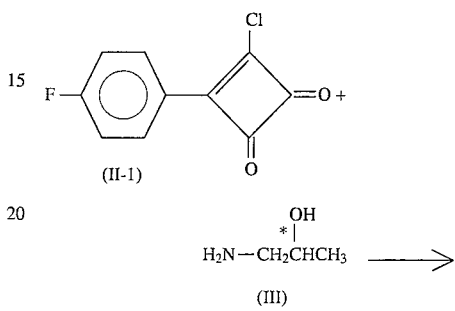

EXAMPLES 14–18

Target products (I-2 to I-6) set forth in Table 4 were synthesized in the same manner as in Examples 1 and 3 except that as the intermediate products there were used cyclobutenedione derivatives (II-6 to II-10) set forth in Table 4, respectively. These target products were subjected to measurement of melting point and maximum absorption wavelength (λmax) in methanol solution and elementary analysis. The results are set forth in Table 5.

TABLE 4

| Example No. | Intermediate product (II) | Target product (I) |
|---|---|---|
| Example 13 | 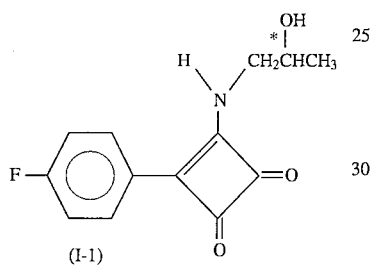 (II-2) | 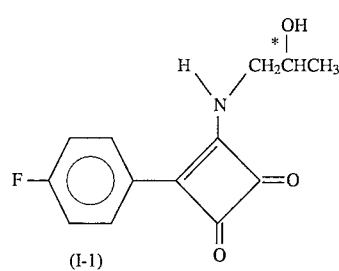 (I-1) |

TABLE 4-continued

| Example No. | Intermediate product (II) | Target product (I) |
|---|---|---|
| Example 14 | (4-Cl-phenyl)-2-ethoxy-cyclobutene-3,4-dione (II-8) | 3-(4-chlorophenyl)-4-(2-hydroxypropylamino)cyclobutene-1,2-dione (I-2) |
| Example 15 | (4-Br-phenyl)-2-ethoxy-cyclobutene-3,4-dione (II-9) | 3-(4-bromophenyl)-4-(2-hydroxypropylamino)cyclobutene-1,2-dione (I-3) |
| Example 16 | (4-I-phenyl)-2-ethoxy-cyclobutene-3,4-dione (II-10) | 3-(4-iodophenyl)-4-(2-hydroxypropylamino)cyclobutene-1,2-dione (I-4) |
| Example 17 | (3,4-diCl-phenyl)-2-chloro-cyclobutene-3,4-dione (II-6) | 3-(3,4-dichlorophenyl)-4-(2-hydroxypropylamino)cyclobutene-1,2-dione (I-5) |
| Example 18 | (2,4-diCl-phenyl)-2-chloro-cyclobutene-3,4-dione (II-7) | 3-(2,4-dichlorophenyl)-4-(2-hydroxypropylamino)cyclobutene-1,2-dione (I-6) |

TABLE 5

| Target product | UV max (nm) | m.p. (°C.) | Elementary analysis | | | | $\beta$ $10^{-30}$ esu | SHG |
|---|---|---|---|---|---|---|---|---|
| | | | C | H | N | halogen | | |
| I-1 | 335.5 322.6 | 213–217° C. | 62.28 (62.65) | 4.90 (4.85) | 5.37 (5.62) | 7.58 (7.62) | 34 | C |
| I-2 | 342.9 328.2 | 204–210° C. | 58.49 (58.77) | 4.53 (4.55) | 5.22 (5.27) | 12.99 (13.34) | 39 | C |
| I-3 | 344.5 329.6 | 205–208° C. | 50.23 (50.34) | 3.64 (3.90) | 4.32 (4.52) | 25.70 (25.76) | 54 | A |
| I-4 | 342.9 328.3 | 208–211° C. | 43.48 (43.72) | 3.29 (3.39) | 3.82 (3.92) | 35.55 (35.53) | 45 | A |
| I-5 | 331.5 347.7 | 242–246° C. | 51.89 (52.02) | 3.71 (3.69) | 4.48 (4.67) | 23.58 (23.62) | 38 | B |
| I-6 | 329.4 | 190–195° C. | 51.97 (52.02) | 3.62 (3.69) | 4.50 (4.67) | 23.54 (23.62) | 31 | C |

EXAMPLE 19

1-(4-Bromophenyl)-2-[(R)-2-hydroxypropylamino]-cyclobutene-3,4-dione [structural formula (I-3)] synthesized in Example 15 was measured for second supramolecular polarizability β in methanol in accordance with Hyper-Rayleigh scattering process proposed by K. Cray, A. Persons et al. [Phys. Rev. Lett., 66 2980, 1991]. The value of β thus obtained was $54 \times 10^{-30}$ esu. On the other hand, a sample comprising p-nitroaniline was measured for second supramolecular polarizability β in the same manner as above. The value of β thus obtained was $34 \times 10^{-30}$ esu.

EXAMPLE 20

The compounds I-1 to I-6 obtained in Examples 13 to 18 were measured for second supramolecular polarizability β in the same manner as in Example 19. The results are set forth in Table 5.

EXAMPLE 21

1-(4-Bromophenyl)-2-[(R)-2-hydroxypropylamino]-cyclobutene-3,4-dione [structural formula (I-3)] synthesized in Example 15 was packed into a glass cell in the form of powder. When the sample was irradiated with Nd-doped YAG laser beam (wavelength: 1.064 μm; output: 180 mJ/pulse), it emitted a scattered green light of 532 nm as a second harmonic of laser. The intensity of the emission was 30 to 50 times that obtained with an urea powder sample.

EXAMPLE 22

Samples were prepared from the compounds (I-2 to I-4) synthesized in Examples 6 to 8. These samples were then measured for optical nonlinearity (SHG activity) as shown below. The results are set forth in Table 5.

For the measurement of SHG activity, an optical system shown in the attached figure was used. Sample 12 was irradiated with light of 1.064 μm from Nd-doped YAG laser 11. A scattered green light of 532 μm emitted by Sample 12 was then passed to photomultiplier 16 through lens 13, filter 14 and monochromator 15 to determine the intensity thereof. In the attached figure, 17 and 18 indicate boxcar integrator and oscilloscope, respectively. The SHG activity of the sample was determined relative to the intensity of an urea powder as a sample. The SHG activity A indicates an activity of more than 10 relative to the urea powder as 1. The SHG activity B indicates a relative activity of 1 to 10. The SHG activity C indicates a relative activity of less than 1.

In accordance with the present invention, a material for nonlinear optical element having a high optical nonlinearity and an excellent heat resistance, weathering resistance, transparency, durability and workability can be provided.

While the invention has been described in detail and with reference to specific embodiments thereof, it will be apparent to one skilled in the art that various changes and modifications can be made therein without departing from the spirit and scope thereof.

What is claimed is:

1. A cyclobutenedione derivative represented by formula (I)

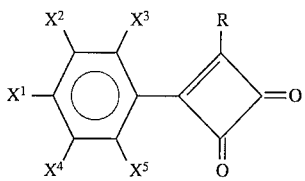

wherein $X^1$ represents a halogen atom; $X^2$, $X^3$, $X^4$ and $X^5$ each represents a hydrogen atom or a halogen atom; and R represents a substituent represented by the following formula

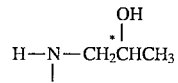

wherein C* represents an asymmetric carbon atom, wherein said carbon atom has an R-configuration or an S-configuration.

2. The cyclobutenedione derivative of claim 1, wherein said cyclobutenedione derivative exhibits a maximum absorption at a wavelength of 35 nm or less.

3. The cyclobutenedione derivative of claim 1, wherein said cyclobutenedione derivative has a second supramolecular polarizability in methanol of about not less than $30 \times 10^{-30}$ esu.

4. A process for preparing a cyclobutenedione derivative represented by formula (I), which comprises reacting a cyclobutenedione derivative represented by formula (II) with an R-configuration or S-configuration of asymmetric 1-amino-2-propanol represented by formula (III):

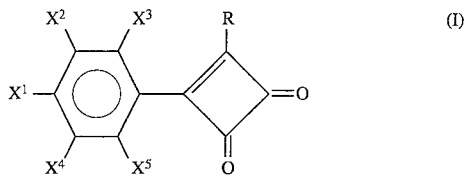

wherein $X^1$ represents a halogen atom; $X^2$, $X^3$, $X^4$ and $X^5$ each represents a hydrogen atom or a halogen atom; and R represents a substituent represented by the following formula

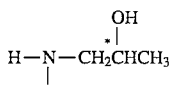

wherein C* represents an asymmetric carbon atom, wherein said carbon atom has an R-configuration or an S-configuration;

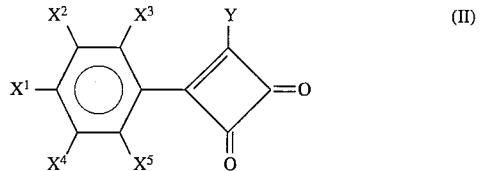

wherein Y represents a chlorine atom, a bromine atom, a methoxy group or an ethoxy group; $X^1$, $X^2$, $X^3$, $X^4$ and $X^5$ each has the same definition as in formula (I);

wherein C* represents an asymmetric carbon atom, wherein said carbon atom has an R-configuration or an S-configuration.

* * * * *